US007691595B2

(12) United States Patent
Fong

(10) Patent No.: US 7,691,595 B2
(45) Date of Patent: Apr. 6, 2010

(54) SENSITIVE IMMUNOCHROMATOGRAPHIC ASSAY

(75) Inventor: Whalley K. Fong, Coquitlam (CA)

(73) Assignee: Response Biomedical Corporation, Vancouver, British Columbia (CA)

(*) Notice: Subject to any disclaimer, the term of this patent is extended or adjusted under 35 U.S.C. 154(b) by 507 days.

(21) Appl. No.: 11/603,281

(22) Filed: Nov. 21, 2006

(65) Prior Publication Data
US 2007/0148717 A1 Jun. 28, 2007

Related U.S. Application Data

(63) Continuation of application No. 10/162,138, filed on Jun. 3, 2002, now Pat. No. 7,175,992, which is a continuation-in-part of application No. 10/120,774, filed on Apr. 10, 2002, now abandoned.

(51) Int. Cl.
G01N 33/533 (2006.01)
(52) U.S. Cl. .................. 435/7.9; 435/7.94; 435/7.1; 435/7.2; 435/287.1; 435/287.9; 435/805; 435/810; 435/970; 436/514; 436/518; 422/100
(58) Field of Classification Search ............. 435/7.94, 435/7.1, 7.2, 287.1, 287.9, 805, 810, 970; 436/514, 518; 422/100
See application file for complete search history.

(56) References Cited

U.S. PATENT DOCUMENTS

| 4,361,537 | A | | 11/1982 | Deutsch et al. | |
|---|---|---|---|---|---|
| 4,806,313 | A | * | 2/1989 | Ebersole et al. | ............... 422/61 |
| 5,141,850 | A | | 8/1992 | Cole et al. | |
| 5,236,826 | A | | 8/1993 | Marshall | |
| 5,356,782 | A | | 10/1994 | Moorman et al. | |
| 5,384,264 | A | | 1/1995 | Chen et al. | |
| 5,415,994 | A | | 5/1995 | Imrich et al. | |
| 5,458,852 | A | | 10/1995 | Buechler | |
| 5,506,114 | A | | 4/1996 | Sangha | |
| 5,569,589 | A | | 10/1996 | Hiraoka et al. | |
| 5,569,608 | A | | 10/1996 | Sommer | |
| 5,602,040 | A | | 2/1997 | May et al. | |
| 5,610,077 | A | | 3/1997 | Davis et al. | |
| 5,622,871 | A | | 4/1997 | May et al. | |
| 5,648,274 | A | | 7/1997 | Chandler | |
| 5,656,503 | A | | 8/1997 | May et al. | |
| 5,753,517 | A | | 5/1998 | Brooks et al. | |
| 5,780,251 | A | | 7/1998 | Klainer et al. | |
| 5,851,048 | A | | 12/1998 | Fujita et al. | |
| 5,885,527 | A | | 3/1999 | Buechler | |
| 5,935,780 | A | | 8/1999 | Naser | |
| 6,103,536 | A | | 8/2000 | Geisberg | |
| 6,121,008 | A | | 9/2000 | Fitzpatrick et al. | |
| 6,133,048 | A | | 10/2000 | Penfold et al. | |
| 6,136,610 | A | | 10/2000 | Polito et al. | |
| 6,187,598 | B1 | | 2/2001 | May et al. | |
| 6,228,660 | B1 | | 5/2001 | May et al. | |
| 6,436,721 | B1 | * | 8/2002 | Kuo et al. | ................... 436/514 |
| 6,482,362 | B1 | * | 11/2002 | Smith | ......................... 422/100 |
| 6,828,110 | B2 | * | 12/2004 | Lee et al. | ..................... 435/7.1 |
| 2002/0082386 | A1 | | 6/2002 | Mangold et al. | |

FOREIGN PATENT DOCUMENTS

| EP | 0 093 613 | | 11/1983 |
|---|---|---|---|
| EP | 0 250 137 | A2 | 8/1987 |
| EP | 0 428 412 | A2 | 5/1991 |
| EP | 0 462 376 | A2 | 12/1991 |
| EP | 0 896 223 | A1 | 2/1999 |
| EP | 1 003 037 | A1 | 5/2000 |
| WO | WO 93/03175 | | 2/1993 |
| WO | WO 97/09620 | | 3/1997 |
| WO | WO 88/08534 | | 11/1998 |
| WO | WO 99/35602 | | 7/1999 |
| WO | WO 99/36780 | | 7/1999 |
| WO | WO 01/50129 | A2 | 7/2001 |

OTHER PUBLICATIONS

Reves, S.G. and Durst, R.A., "Novel Optical Measurement Approach for the Quantification of Liposome Immunomigration Assays," *Analytical Letters*, 28(13): 2347-2362 (1995).

Borque, L., et al., "Automated Quantitative Nephelometric Latex Immunoassay for Determining Ferritin in Human Serum," *J. Clin. Lab. Analysis*, 6: 239-244 (1992).

Roberts, M.A. and Durst, R.A., Investigation of Liposome-Based Immunomigration Sensors for the Detection of Polychlorinated Biphenyls,: *Analytical Chem.* 67:482-491 (1995).

(Continued)

Primary Examiner—Bao-Thuy L Nguyen
(74) Attorney, Agent, or Firm—Hamilton, Brook, Smith & Reynolds, P.C.

(57) ABSTRACT

Methods for quantitatively measuring the amount of an analyte of interest in a fluid sample, and kits useful in the methods, are disclosed. The methods involve providing a solid phase apparatus comprising a membrane having an application point, a sample capture zone, and a control capture zone, where the sample capture region is between the application point and the control capture zone; and providing a sample collection apparatus comprising a population of analyte binding particles or a population of analyte coated particles. In the assays, a fluid sample is introduced into the sample collection apparatus, and the resultant mixture is applied to the application point of the membrane. The fluid allows transport components of the assay by capillary action to and through the sample capture zone and subsequently to and through the control capture zone. The amount of analyte in the fluid sample is related (e.g., either directly or inversely) to a corrected particle amount, which can be determined, for example, as a ratio of the amount of particles in the sample capture zone and the amount of particles in the control capture zone.

22 Claims, No Drawings

OTHER PUBLICATIONS

Siebert, S.T.A., et al., Lipsome Immunomigration Field Assay Device for Alachlor Determination, *Analytica Chimica Acta*, 282:297-305 (1993).

Siebert, R.S., et al., "Improved Liposome Immunomigration Strip Assay for Alachlor Determination," *Analytica Chimica Acta*, 311:309-318(1995).

Schifreen, R.S., et al., "A Quantitative Automated Immunoassay for Fibrinogen/Fibrin Degradation Products," *Clin. Chem.*, 31(9): 1468-1473 (1985).

Laitinen, M.P.A. and Vuento, M., "Immunochromatographic Assay for Quantitation of Milk Progesterone," *Acta Chemica Scandinavica*, 50:141-145 (1996).

Findlay, J.W.A., et al., "Validation of Immunoassays for Bioanalysis: a Pharmaceutical Industry Perspective," *Journal of Pharmaceutical and Biomedical Analysis*, 21(6): 1249-1273 (2000).

Paek, S.H., et al., "Development of Rapid One-Step Immunochromatographic Assay," *Methods*, 22(1): 53-60 (2000).

Fitzpatrick, J. et al., "7C Gold Urinary Assay of Neural Thread Protein in Alzheimer's Disease," *Alzheimer's Reports*, 3: 155-159 (2000).

* cited by examiner

SENSITIVE IMMUNOCHROMATOGRAPHIC ASSAY

RELATED APPLICATIONS

This application is a continuation of U.S. application Ser. No. 10/162,138, filed Jun. 3, 2002, now U.S. Pat. No. 7,175,992 which is a continuation-in-part of U.S. application Ser. No. 10/120,774, filed Apr. 10, 2002, now abandoned the entire teachings which are incorporated herein by reference.

BACKGROUND OF THE INVENTION

Quantitative analysis of cells and analytes in fluid samples, particularly bodily fluid samples, often provides critical diagnostic and treatment information for physicians and patients. Quantitative immunoassays utilize the specificity of the antigen (Ag)-antibody (Ab) reaction to detect and quantitate the amount of an Ag or Ab in a sample. In solid phase immunoassays, one reagent (e.g., the Ag or Ab) is attached to a solid surface, facilitating separation of bound reagents or analytes from free reagents or analytes. The solid phase is exposed to a sample containing the analyte, which binds to its Ag or Ab; the extent of this binding is quantitated to provide a measure of the analyte concentration in the sample. Transduction of the binding event into a measurable signal, however, is affected by a number of limitations, including constraints of particle movement on the solid phase, which affect the specificity and applicability of quantitative immunoassays.

SUMMARY OF THE INVENTION

The invention relates to methods of measuring the amount of an analyte of interest in a fluid sample, using a solid phase assay (e.g., a sandwich immunoassay or an inhibition immunoassay), in which an analyte of interest and a capture reagent are used as part of a specific binding pair; and to kits for use in the methods.

In the methods of the invention, a solid phase apparatus is provided, which includes a membrane strip having an application point, a sample capture zone and a control capture zone; the sample capture zone is between the application point and the control capture zone. A sample capture reagent (e.g., an agent that binds to the analyte of interest, such as an antibody to the analyte of interest) is immobilized in the sample capture zone. A control capture reagent (e.g., an agent that binds to the analyte binding particles, such as an anti-immunoglobulin antibody) is immobilized in the control capture zone. Also provided is a sample collection apparatus containing a population of particles, such as liposomes, colloidal gold, or organic polymer latex particles, stored in a stable form.

In "sandwich" immunoassays of the invention, the particles are "analyte binding" particles that are coated with a binding agent (e.g., an antibody) to the analyte of interest. In "competitive" or "inhibition" assays, the particles are "analyte coated" particles that are coated with analyte of interest. In either type of assay, the particles can be labeled, using a colorimetric, fluorescent, luminescent, chemiluminescent, or other appropriate label, to facilitate detection.

In one embodiment of the methods, a fluid sample to be assessed for the analyte of interest is introduced into the sample collection apparatus, and a buffer is subsequently introduced into the mixed fluid sample. In another embodiment of the methods, a buffer is introduced into the sample collection apparatus, and the fluid sample to be assessed for the analyte of interest is subsequently introduced. In a third embodiment of the methods, the fluid sample is formed by introducing a solid into a buffer, and the fluid sample is subsequently introduced into the sample collection apparatus. In any of these embodiments, a buffered, mixed fluid sample containing the particles is produced.

In a sandwich assay, analyte of interest present in the sample interacts with the analyte binding particles, resulting in contacted analyte binding particles within the mixed fluid sample. The buffered, mixed fluid sample is applied to the application point of the membrane strip of the solid phase apparatus. The solid phase apparatus is then maintained under conditions which are sufficient to allow capillary action of fluid to transport particles to and through the sample capture zone.

The sample capture reagent interacts with contacted analyte binding particles, resulting in arrest of particles in the sample capture zone. Capillary action of the fluid further mobilizes the contacted analyte binding particles not only to and through the sample capture zone, but also to and through the control capture zone, where they bind to the control capture reagent. Capillary action of the fluid continues to mobilize the remaining unbound particles past the control capture zone (e.g., into a wicking pad). The amount of analyte binding particles that are arrested in the sample capture zone, and in the control capture zone, are then determined.

The amount of analyte of interest in the fluid sample is then determined. For example, the amount of analyte of interest in the fluid sample can be determined as a ratio between 1) the amount of analyte binding particles that are arrested in the sample capture zone, and 2) the amount of analyte binding particles in the control capture zone. Alternatively, the amount of analyte of interest in the fluid sample can be determined as a ratio between 1) the amount of analyte binding particles that are arrested in the sample capture zone, and 2) the sum of the amount of analyte binding particles in the control capture zone and the amount of analyte binding particles that are arrested in the sample capture zone.

In a competitive or inhibition type of assay, the buffered, mixed fluid sample is applied to the application point of the membrane strip of the solid phase apparatus. The solid phase apparatus is then maintained under conditions which are sufficient to allow capillary action of fluid to transport particles to and through the sample capture zone.

The sample capture reagent interacts with analyte-coated particles; interaction of the sample capture reagent and the analyte-coated particles results in arrest of analyte-coated particles in the sample capture zone. Because of competition between the analyte-coated particles and analyte (if present) in the sample for binding sites on the sample capture reagent in the sample capture zone, the amount of analyte-coated particles arrested in the sample capture zone is inversely proportional to the amount of analyte in the sample. Capillary action of the fluid further mobilizes the analyte-coated particles not only to the sample capture zone, but also to the control capture zone, where they bind to the control capture reagent. The amount of analyte-coated particles that are arrested in the sample capture zone, and in the control capture zone, are then determined.

The amount of analyte of interest in the fluid sample is then determined. For example, the amount of analyte of interest in the fluid sample is inversely related to a ratio between 1) the amount of analyte-coated particles that are arrested in the sample capture zone, and 2) the amount of analyte-coated particles in the control capture zone. Alternatively, the amount of analyte of interest in the fluid sample is inversely related to a ratio between 1) the amount of analyte-coated particles that are arrested in the sample capture zone, and 2)

the sum of the amount of analyte-coated particles in the control capture zone and the amount of analyte-coated particles that are arrested in the sample capture zone.

The flow of fluid through a solid phase in such quantitative assays contributes to the dynamic nature of the assays: the amount of analyte binding to particles, as well as the location of particles in relation to positions on the solid phase, is in flux. The structure of the solid phase reactants, as well as the viscosity of the fluid sample and other factors, can thereby contribute to limitations on specificity of the assays. The methods of the invention reduce certain constraints on the dynamic nature of the assays, thereby allowing more accurate determination of the amounts of analytes of interest in solutions. For example, in the sandwich assays, because the fluid sample to be assayed for the analyte of interest is mixed with the analyte binding particles prior to application to the membrane, there is a longer time for the analyte of interest to bind to the analyte binding particles prior to the capture reaction which occurs in the membrane. Furthermore, because the interaction between the analyte of interest and the analyte binding particles occurs in the fluid phase, there is faster and more efficient binding because of greater mobility of the particles, than there would be in the same interaction between analyte of interest and analyte binding particles in the matrix of the membrane of the solid phase apparatus. In both the sandwich assays and the inhibition (competitive) assays, it is possible to increase the volume of particles used without overloading the membrane, thereby increasing sensitivity of the assay. In addition, the particles pass over the capture zones in a continuous manner through the capillary action of the fluid, rather than in a quick wave on the crest of a fluid front, allowing more effective capture of particles and thereby enhancing sensitivity of the assays.

DETAILED DESCRIPTION OF THE INVENTION

The present invention pertains to methods of quantitatively measuring the amount of an analyte using assays, particularly quantitative immunochromatographic assays, and kits therefor.

An "assay," as used herein, refers to an in vitro procedure for analysis of a sample to determine the presence, absence, or quantity of one or more analytes. The assays of the inventions utilize an analyte and an analyte binding agent. The analyte and the analyte binding agent are members of a specific "binding pair," in which a first member of the binding pair (e.g., analyte) reacts specifically with a second member (e.g., the binding agent). One or both members of the binding pair can be an antibody. For example, a first member of the binding pair (e.g., an analyte of interest) can be an antibody, and a second member of the binding pair (e.g., a binding agent) can be anti-immunoglobulin antibody; alternatively, the first member of the binding pair (e.g., the analyte) can be an antigen, and the second member of the binding pair (e.g., the binding agent) can be an antibody.

In one embodiment, the assay is an "immunoassay" which utilizes antibodies as a component of the procedure. In a preferred embodiment, the immunoassay is a "sandwich" assay, which is a test for an analyte in which a fluid sample to be assessed for the presence or absence, or quantity of analyte, is contacted with particles coated with an analyte binding agent, such as antibodies to the analyte, and the resultant mixture is applied to a membrane and subsequently moves by capillary action through the membrane. A positive result is indicated by detection of interaction between analyte and analyte binding agent-coated particles in a capture zone of the membrane, the amount of analyte binding agent-coated particles in the capture zone being related to the amount of analyte in the fluid sample. In another preferred embodiment, the immunoassay is an "inhibition" or "competitive" assay, which is a test for an analyte in which a fluid test sample to be assessed for the presence or absence, or quantity of analyte, is contacted with particles coated with the analyte, and the resultant mixture is applied to a membrane and subsequently moves by capillary action the system through the membrane. A positive result is indicated by detection of interaction between analyte binding agent and analyte-coated particles in a capture zone of the membrane, the amount of analyte-coated particles in the capture zone being inversely related to the amount of analyte in the fluid sample.

In another embodiment of the assays of the invention, neither the analyte nor the binding agent are antibodies: for example, the first member of the binding pair can be a ligand, and the second member of the binding pair can be a receptor; alternatively, the first member of the binding pair can be a lectin, and the second member of the binding pair can be a sugar. In still another embodiment, the first member of the binding pair can be a nucleic acid (e.g., DNA, RNA), and the second member of the binding pair can be a nucleic acid which specifically hybridizes to the first member of the binding pair. "Specific hybridization," as used herein, refers to the ability of a first nucleic acid to hybridize to a second nucleic acid in a manner such that the first nucleic acid does not hybridize to any nucleic acid other than to the second nucleic acid (e.g., when the first nucleic acid has a higher similarity to the second nucleic acid than to any other nucleic acid in a sample wherein the hybridization is to be performed). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 70%, 75%, 80%, 85%, 90%, 95%). For example, certain high stringency conditions can be used which distinguish perfectly complementary nucleic acids from those of less complementarity. "High stringency conditions", "moderate stringency conditions" and "low stringency conditions" for nucleic acid hybridizations are explained on pages 2.10.1-2.10.16 and pages 6.3.1-6.3.6 in *Current Protocols in Molecular Biology* (Ausubel, F. M. et al., "*Current Protocols in Molecular Biology*", John Wiley & Sons, (1998), the entire teachings of which are incorporated by reference herein). The exact conditions which determine the stringency of hybridization depend not only on ionic strength (e.g., 0.2×SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, equivalent conditions can be determined by varying one or more of these parameters while maintaining a similar degree of identity or similarity between the two nucleic acid molecules.

Regardless of the composition of the analyte and the binding agent, these two components nevertheless form a specific binding pair, in which the first member reacts specifically with the second member. Specific interaction between the members of the binding pair indicates that the first member of the binding pair preferentially binds or otherwise interacts with the second member of the binding pair, preferably to the exclusion of any binding to another compound in the assay.

The terms, "analyte" or "analyte of interest," as used herein, refer to a first member of a binding pair as described above. The analyte is a molecule or compound for which the amount will be measured. The analyte can be in the form of a solid, such as a dry substance (e.g., a powder, a particulate; spore; or other particle), or can be in the form of a fluid (e.g., a solid as described above that has been dissolved or suspended in a fluid; or other liquid sample). Examples of analytes include spores; proteins, such as hormones or enzymes; glycoproteins; peptides; small molecules; polysaccharides; antibodies; nucleic acids; drugs; toxins (e.g., environmental toxins); viruses or virus particles; portions of a cell wall; and other compounds. In a preferred embodiment, the analyte is "immunogenic," which indicates that antibodies (as described below) can be raised to the analyte, or to an analyte that is bound to a carrier (e.g., a hapten-carrier conjugate, for which antibodies can be raised to the hapten). In some representative embodiments, the analyte of interest can be myoglobin; CK-MB; troponin I; PSA; digoxin; theophylline; a hormone (e.g., T-3 or T-4); a drug of abuse (LSD, THC, barbituates, etc.); or a spore of *Bacillus anthracis* (anthrax). The analyte of interest can be in a liquid sample; alternatively, the analyte of interest can be in a dry (non-fluid) sample (e.g., a solid, such as a particulate sample, powder sample, or soil sample).

In the methods of the invention, a fluid sample is assessed for the presence or absence, or quantity, of an analyte of interest. The fluid can be a fluid that wets the membrane material; that supports a reaction between the analyte of interest and the analyte binding agent, such as the antibody/antigen reaction (i.e., does not interfere with antibody/antigen interaction); and that has a viscosity that is sufficiently low to allow movement of the fluid by capillary action. In a preferred embodiment, the fluid is an aqueous solution (such as a bodily fluid). The fluid sample can be a fluid having relatively few components, for example, an aqueous solution containing the analyte of interest; alternatively, the fluid sample can be a fluid having many components, such as a complex environmental sample (e.g., sewage, waste water, groundwater, or other water sample), or a complex biological fluid (e.g., whole blood, plasma, serum, urine, cerebrospinal fluid, saliva, semen, vitreous fluid, synovial fluid, or other biological fluid). In a preferred embodiment in which the fluid is a biological fluid, the fluid is whole blood, plasma, or serum. If desired, the fluid sample can be diluted; for example, if a complex biological fluid is used as the fluid sample, it can be diluted with a solution (e.g., an aqueous solution).

If the analyte of interest is not in solution (e.g., the analyte of interest is in a dry or solid sample, as described above), it can be extracted, suspended, or dissolved into a fluid sample first. For example, if the analyte of interest is a nucleic acid, it can be extracted from cells of interest into a solution (e.g., an aqueous solution, such as the buffer described below); in another example, if the analyte of interest is a powder or particulate material (e.g., a powder, a particulate, a soil sample, or spores), it can be suspended or dissolved into a solution (e.g., an aqueous solution, such as the buffer described below) such as by obtaining a sample of the dry material (e.g., using a swab or other instrument) and placing the sample of dry material into the solution. Thus, a "fluid sample" can refer not only to a liquid sample to be assessed for an analyte of interest, but also to a fluid sample in which a solid material (to be assessed for an analyte of interest) is extracted, suspended or dissolved.

The "analyte binding agent," as used herein, refers to second member of a binding pair as described above. The analyte binding agent is a compound that specifically binds to the analyte (the first member of the binding pair), such as an antibody, a hapten or drug conjugate, a receptor, or another binding partner. In a preferred embodiment, the analyte binding agent is an antibody to the analyte of interest.

Sandwich Assays

The "sandwich" assay of the invention utilizes a solid phase apparatus. The solid phase apparatus includes a membrane strip having an application point, a sample capture zone, and a control capture zone. The solid phase apparatus may optionally include a wicking pad following the control capture zone, and a sample pad adjacent to or covering the application point. The membrane strip can be made of a substance having the following characteristics: sufficient porosity to allow capillary action of fluid along its surface and through its interior; the ability to allow movement of coated particles (e.g., analyte binding particles, as described below) or complexes of particles and analyte of interest (e.g., contacted analyte binding particles, as described below) by capillary action (i.e., it must not block the particles or complexes of particles and analyte of interest); and the ability to be wet by the fluid containing the analyte (e.g., hydrophilicity for aqueous fluids, hydrophobicity for organic solvents). Hydrophobicity of a membrane can be altered to render the membrane hydrophilic for use with aqueous fluid, by processes such as those described in U.S. Pat. No. 4,340,482, or U.S. Pat. No. 4,618,533, which describe transformation of a hydrophobic surface into a hydrophilic surface. Examples of membrane substances include: cellulose, cellulose nitrate, cellulose acetate, glass fiber, nylon, polyelectrolyte ion exchange membrane, acrylic copolymer/nylon, and polyethersulfone. In a preferred embodiment, the membrane strip is made of cellulose nitrate (e.g., a cellulose nitrate membrane with a Mylar backing).

The "application point" is the position on the membrane where a fluid can be applied. An "application pad" can also optionally be used; the application pad rests on the membrane, immediately adjacent to or covering the application point. The application pad can be made of an absorbent substance which can deliver a fluid sample, when applied to the pad, to the application point on the membrane. Representative substances include cellulose, cellulose nitrate, cellulose acetate, nylon, polyelectrolyte ion exchange membrane, acrylic copolymer/nylon, polyethersulfone, or glass fibers. In one embodiment, the pad is a Hemasep®-V pad (Pall Corporation). In another embodiment, the pad is a glass fiber pad. If a wicking pad is present, it can similarly be made from such absorbent substances.

The "sample capture zone" refers to a point on the membrane strip at which a "sample capture reagent" is immobilized (e.g., coated on and/or permeated through the membrane). The sample capture reagent is an analyte binding agent, such as those described above. The sample capture reagent need not be the same analyte binding agent as described above; however, the sample capture reagent also forms a binding pair with the analyte of interest, in that it specifically and preferentially binds to the analyte of interest. In a preferred embodiment, the sample capture reagent is an antibody directed against the analyte; it can be directed against the same epitope of the analyte as, or against a different epitope of the analyte from, the epitope that binds to the antibodies used as analyte binding agents coated on the particles.

The apparatus additionally includes a "control capture reagent" immobilized in a "control capture zone." The control capture reagent is a reagent which reacts with the analyte binding particles, but which does not interact with the analyte to be measured: for example, the control capture reagent can react with the analyte binding agent on the analyte binding agent-coated particles; with another material on the particles; or with the particles themselves. For example, if the analyte binding agent is an antibody, the control capture reagent can be an anti-immunoglobulin antibody. In a preferred embodiment, the analyte binding agent is an antibody, and the control capture reagent is an anti-immunoglobulin antibody. The control capture reagent is immobilized on the membrane (coated on and/or permeated in the membrane) in a control capture zone.

The control capture zone is positioned such that the sample capture zone is between the application point and the control capture zone. In a preferred embodiment, the control capture zone is closely adjacent to the sample capture zone, so that the dynamics of the capillary action of the components of the assay are similar (e.g., essentially the same) at both the control capture zone and the sample capture zone. Although they are closely adjacent, the control capture zone and the sample capture zone are also sufficiently spaced such that the particles arrested in each zone can be quantitated individually (e.g., without cross-talk). Furthermore, in a preferred embodiment, the sample capture zone is separated from the application point by a space that is a large distance, relative to the small distance between the sample capture zone and the control capture zone. The speed of the capillary front (the border of the fluid moving through the membrane by capillary action) is inversely related to the distance of the capillary front from the application point of the fluid. Because particle capture is a rate limiting step in the assay, the distance between the application point (where the capillary front mobilizes analyte binding particles) and the capture zones (where particles are captured) must be sufficient to retard the speed of the capillary front to a rate that is slow enough to allow capture of particles when the capillary front reaches the sample capture zone. In addition, the distance must be sufficiently large so that the total time of migration (movement of the capillary front through the entire membrane) is long enough to allow free analyte in a fluid sample to bind to analyte binding particles. The optimal distances between the components on the membrane strip can be determined and adjusted using routine experimentation.

The quantitative assay additionally uses a sample collection apparatus. A "sample collection apparatus," as used herein, refers to an apparatus that can be used for collection of the fluid sample or into which a collected fluid sample can be deposited or stored. The sample collection apparatus can be any apparatus which can contain the analyte binding particles, as described below, and which to which can be added a measured volume of fluid sample. Representative sample collection apparatus include a sample tube, a test tube, a vial, a pipette or pipette tip, a syringe. In a preferred embodiment, the sample collection apparatus is a pipette or pipette tip.

The sample collection apparatus contains a population of "analyte binding particles" which are coated with the analyte binding agent. The population of particles varies, depending on the size and composition of the particles, the composition of the membrane of the solid phase apparatus, and the level of sensitivity of the assay. The population typically ranges approximately between $1 \times 10^3$ and $1 \times 10^9$, although fewer or more can be used if desired. In a preferred embodiment, the population is approximately $2 \times 10^8$ particles.

The analyte binding particles are particles which can be coated with the analyte binding agent (the second member of the binding pair). In a preferred embodiment, the analyte binding particles are liposomes, colloidal gold, organic polymer latex particles, inorganic fluorescent particles or phosphorescent particles. In a particularly preferred embodiment, the particles are polystyrene latex beads, and most particularly, polystyrene latex beads that have been prepared in the absence of surfactant, such as surfactant-free Superactive Uniform Aldehyde/Sulfate Latexes (Interfacial Dynamics Corp., Portland, Oreg.).

The size of the particles is related to porosity of the membrane (for analytes in fluid samples) and also to the size of the analyte of interest (e.g., for particulate analytes): the particles must be sufficiently small to be transported along the membrane by capillary action of fluid, and also (for solid, e.g., particulate analytes, sufficiently small for the complex of contacted analyte binding particles, as described below, to be transported along the membrane by capillary action). The particles can be labeled to facilitate detection. The particles are labeled by a means which does not significantly affect the physical properties of the particles; for example, the particles are labeled internally (that is, the label is included within the particle, such as within the liposome or inside the polystyrene latex bead). Representative labels include luminescent labels; chemiluminescent labels; phosphorescent labels; enzyme-linked labels; chemical labels, such as electroactive agents (e.g., ferrocyanide); and colorimetric labels, such as dyes or fluorescent labels. In one embodiment, a fluorescent label is used. In another embodiment, phosphorescent particles are used, particularly "up-converting" phosphorescent particles, such as those described in U.S. Pat. No. 5,043,265.

The particles are coated with an analyte binding agent that is a second member of the binding pair. As described above, the analyte binding agent (second member of the binding pair) specifically and preferentially binds to the analyte of interest (first member of the binding pair). Representative analyte binding agents include antibodies (or fragments thereof); haptens; drug conjugates; receptors; or other binding partners. In one preferred embodiment, the analyte binding agent is an antibody to the analyte of interest. Antibodies can be monoclonal antibodies or polyclonal antibodies. The term "antibody", as used herein, also refers to antibody fragments which are sufficient to bind to the analyte of interest. Alternatively, in another embodiment, molecules which specifically bind to the analyte of interest, such as engineered proteins having analyte binding sites, can also be used (Holliger, P. and H. R. Hoogenbloom, *Trends in Biotechnology* 13:7-9 (1995); Chamow, S. M. and A. Ashkenazi, *Trends in Biotechnology* 14:52-60:1996)). In still another embodiment, if the analyte of interest is a drug, a hapten or other drug conjugate can be used as the analyte binding agent. Alternatively, in a further embodiment, a receptor which binds to the analyte can be used (e.g., if the analyte of interest is a ligand). If the analyte is an antibody of known specificity, the particles can be coated with the antigen against which the analyte-antibody is directed, or can be coated with antibody to the analyte-antibody. Furthermore, because the analyte and the analyte binding agent form a binding pair, compounds or molecules described as representative analytes can also serve as analyte binding agents, and those described as representative analyte binding agents can similarly serve as analytes, as described herein.

The analyte binding particles contained within the sample collection apparatus are stored in a stable form within the sample collection apparatus. A "stable form," as the term is used herein, indicates a form in which the particles do not significantly change in chemical makeup or physical state during storage. The stable form can be a liquid, gel, or solid form. In preferred embodiments, the analyte binding particles contained within the sample collection apparatus are evaporatively dried; freeze-dried; and/or vacuum-dried.

In a particularly preferred embodiment, the sample collection apparatus is a pipette tip in which are vacuum-dried analyte binding particles.

To perform the assay, a fluid sample to be assessed for the presence of the analyte of interest, as described above, is used. In one embodiment, the fluid sample is introduced into (drawn into, poured into, or otherwise placed into) the sample collection apparatus. For example, in one embodiment, the fluid sample is drawn up into a sample collection apparatus that comprises a pipette tip. Introduction of the fluid sample into the sample collection apparatus results in mixing of the fluid sample with the analyte binding particles, forming a "mixed fluid sample." If the analyte binding particles are evaporatively-, freeze- or vacuum-dried, the introduction of the fluid sample into the sample collection apparatus can result in rehydration and suspension of the analyte binding particles in the fluid sample. A buffer (e.g, for dilution) is also introduced into the mixed fluid sample, forming a "buffered, mixed fluid sample." The buffered, mixed fluid sample can be formed either by dispensing the mixed fluid sample into a "buffer container" (e.g., test tube) containing the buffer, or by introducing the buffer into the sample collection apparatus prior to introducing the fluid sample. Alternatively, if the analyte of interest is a solid (e.g., a powder, a particulate; spore; or other particle, as described above), the fluid sample as described above can be prepared by introducing the solid into the buffer container; in this embodiment, the buffered, mixed fluid sample is formed by introducing the fluid sample (comprising the buffer) into the sample collection apparatus. In another embodiment, the buffer is introduced into the sample collection apparatus, followed by introduction of the fluid sample into the sample collection apparatus.

The buffer can be an aqueous fluid that supports a reaction between the analyte of interest and the analyte binding agent (e.g., does not interfere with antibody/antigen interaction); and that has a viscosity that is sufficiently low to allow movement of the fluid by capillary action. In one embodiment, the buffer contains one or more of the following components: a buffering agent (e.g., phosphate); a salt (e.g., NaCl); a protein stabilizer (e.g., BSA, casein, serum); and/or a detergent such as a nonionic detergent or a surfactant (e.g., one or more of the following agents commonly available in surfactant tool kits: NINATE 411, Zonyl FSN 100, Aerosol OT 100%, GEROPON T-77, BIO-TERGE AS-40, STANDAPOL ES-1, Tetronic 1307, Surfnyol 465, Surfynol 485, Surfynol 104PG-50, IGEPAL CA210, TRITON X-45, TRITON X-100, TRITON X305, SILWET L7600, RHODASURF ON-870, Cremophor EL, TWEEN 20, TWEEN 80, BRIJ 35, CHEMAL LA-9, Pluronic L64, SURFACTANT 10G, SPAN 60, CREL). Optionally, if desired, the buffer can contain a thickening agent. Such components for buffers are commercially available. Representative buffers include, for example, saline, or 50 mM Tris-HCl, pH 7.2. Alternatively, water can be used in lieu of a buffered solution; as used herein, the term "buffer" refers to either a buffered solution or to water.

To disperse the analyte binding particles further into the fluid sample, if desired, the sample collection apparatus into which the fluid sample and the buffer has been introduced, or the buffer container into which the mixed fluid sample has been introduced, can be agitated (e.g., vortexed, shaken, pipetted down and up, etc.).

In a preferred embodiment, the sample collection apparatus comprises a pipette tip having vacuum-dried analyte binding particles within its tip; the fluid sample is drawn into the pipette, thereby rehydrating the dried analyte binding particles and forming a mixed fluid sample. In a particularly preferred embodiment, the mixed fluid sample is introduced into a buffer container, resulting in a buffered mixed fluid sample; the buffered mixed fluid sample in the buffer container is pipetted up and down using the sample collection apparatus, thereby further dispersing the analyte binding particles.

If analyte of interest is present in the buffered, mixed fluid sample, binding occurs between the analyte and the analyte binding particles. "Binding" of analyte to the analyte binding particles indicates that the analyte binding agent coated onto the particle is interacting with (e.g., binding to) analyte of interest. Analyte binding particles which have been maintained (incubated) under conditions allowing analyte in the fluid (if present) to bind to the analyte binding particles immobilized in the application point are referred to herein as "contacted analyte binding particles". Contacted analyte binding particles may or may not have analyte bound to the analyte binding agent, depending on whether or not analyte is present in the fluid sample and whether analyte has bound to the analyte binding agent on the analyte binding particles. Because there are multiple binding sites for analyte on the analyte binding particles, the presence and the concentration of analyte bound to analyte binding particles varies; the concentration of analyte bound to the analyte binding particles increases proportionally with the amount of analyte present in the fluid sample, and the probability of an analyte binding particle being arrested in the sample capture zone (as described below) similarly increases with increasing amount of analyte bound to the analyte binding particles. Thus, the population of contacted analyte binding particles may comprise particles having various amount of analyte bound to the analyte binding agent, as well as particles having no analyte bound to the analyte binding agent (just as the analyte binding particles initially have no analyte bound to the analyte binding agent). Furthermore, the degree of binding increases as the time factor of the conditions increases: while the majority of binding occurs within one minute (e.g., 60 seconds, preferably less than 60 seconds (e.g., 45 seconds, 30 seconds, or less), additional incubation (e.g., more than one minute (2 minutes, 5 minutes, 10 minutes, 15 minutes) results in additional binding.

The buffered, mixed fluid sample is applied to the application point of the membrane strip of the solid phase apparatus, or to the application pad, if present. After the membrane strip is contacted with the buffered, mixed fluid sample, the membrane strip is maintained under conditions which allow fluid to move by capillary action to and through the membrane. The contacted analyte binding particles move through the membrane as a result of capillary action of the fluid from the buffered, mixed fluid sample, and the contacted analyte binding particles move along the membrane to and through the "sample capture zone" on the membrane and subsequently to and through the "control capture zone." The membrane strip is maintained under conditions (e.g., sufficient time and fluid volume) which allow the contacted analyte binding particles to move by capillary action along the membrane to and through the sample capture zone and subsequently to the control capture zone, and subsequently beyond the capture zones (e.g., into a wicking pad), thereby removing any nonbound particles from the capture zones.

The movement of some of the contacted analyte binding particles is arrested by binding of contacted analyte binding particles to the sample capture reagent in the sample capture zone and subsequently by binding of some of the contacted analyte binding particles to the control capture reagent in the control capture zone. In one preferred embodiment, the analyte binding agent is antibody to the antigen of interest, and the control capture reagent can be antibody against immunoglobulin of the species from which the analyte binding agent is derived. In this embodiment, the antibody to immunoglobulin should be non-cross reactive with other components of the sample: for example, if a human sample is being tested, an antibody that does not react with human immunoglobulin can be used as the control capture reagent.

Sample capture reagent binds to contacted analyte binding particles by binding to analyte which is bound to analyte binding agent on the contacted analyte binding particles. The term, "sample-reagent-particle complexes", as used herein, refers to a complex of the sample capture reagent and contacted analyte binding particles. Contacted analyte binding particles are arrested in the sample capture zone, forming the sample-reagent-particle complexes, due to capture of contacted analyte binding particles by interaction of analyte with sample capture reagent in the sample capture zone.

Control capture reagent binds to contacted analyte binding particles by binding to analyte binding agent on the contacted analyte binding particles. The term, "control-reagent-particle complexes," as used herein, refers to a complex of the control capture reagent and contacted analyte binding particles. Contacted analyte binding particles are arrested in the control capture zone, forming the control-reagent-particle complexes, due to capture of contacted analyte binding particles by interaction of analyte binding particles with control capture reagent in the control capture zone. As indicated above, the control capture reagent interacts with the analyte binding particles (e.g., with the analyte binding agent on the analyte binding agent-coated particles, or another material on the particles, or with the particles themselves), but not with the analyte itself.

Capillary action subsequently moves any contacted analyte binding particles that have not been arrested in either the sample capture zone or the control capture zone, onwards beyond these zones, thereby removing any particles that have not been arrested.

In a preferred embodiment, the fluid moves any contacted analyte binding particles that have not been arrested, into a wicking pad which follows the control capture zone.

If desired, a secondary wash step can be used. A buffer (e.g., the buffer described above) can be applied at the application point after the buffered, mixed fluid sample has soaked in to the membrane or into the application pad, if present. The secondary wash step can be used at any time thereafter, provided that it does not dilute the buffered, mixed fluid sample. A secondary wash step can contribute to reduction of background signal when the analyte binding particles are detected, as described below.

The amount of analyte binding particles arrested in the sample capture zone (sample-reagent-particle complexes) is then detected using an appropriate means for the type of label used on the analyte binding particles. In a preferred embodiment, the amount is detected by an optical method, such as by measuring the amount of fluorescence of the label of the analyte binding particles. Alternatively, the amount of sample-reagent-particle complexes can be detected using electrical conductivity or dielectric (capacitance). Alternatively, electrochemical detection of released electroactive agents, such as indium, bismuth, gallium or tellurium ions, as described by Hayes et al. (*Analytical Chem.* 66:1860-1865 (1994)) or ferrocyanide as suggested by Roberts and Durst (*Analytical Chem.* 67:482-491 (1995)) can be used. For example, if liposomes are used, ferrocyanide encapsulated within the liposome can be released by addition of a drop of detergent at the capture zone, and the released ferrocyanide detected electrochemically (Roberts and Durst, id). If chelating agent-protein conjugates are used to chelate metal ions, addition of a drop of acid at the capture zone will release the ions and allow quantitation by anodic stripping voltametry (Hayes et al., id.). Similarly, the amount of analyte binding particles arrested in the control capture zone is detected in the same manner as the amount of analyte binding particles in the sample capture zone.

In one embodiment, the detected amount of analyte binding particles is represented by a curve that is directly related to the amount of label present at positions along the solid phase (e.g., the membrane strip). For example, the detected amounts of particles at each position on the membrane strip (e.g., at the sample capture zone and the control capture zone, and/or areas in between or adjacent to the sample capture zone and the control capture zone, and/or other areas of the membrane strip) can be determined and plotted as a function of the distance of the position along the membrane strip. The amount of particles can then be calculated as a function of the area under the curve, which is related to the amount of label present.

A corrected analyte binding particle amount is then determined, and the amount of analyte can then be determined from the corrected analyte binding particle amount using appropriate calculation. The corrected analyte binding particle amount is based on the amount of analyte binding particles arrested in the sample capture zone and in the control capture zone. For example, in one embodiment, the corrected analyte binding particle amount is determined as a ratio (R) of the analyte binding particle amount present in the sample capture zone to the analyte binding particle amount present in the control capture zone. The amount of analyte present can be then determined from the corrected analyte binding particle amount (the ratio), utilizing a standard curve. The standard curve is generated by preparing a series of control samples, containing known concentrations of the analyte of interest in the fluid in which the analyte is to be detected (for example, such as serum depleted of the analyte). The assay is then performed on the series of control samples; the value of R is measured for each control sample; and the R values are plotted as a function of the concentration of analyte included in the control sample. Samples containing an unknown amount of analyte (the "test samples") are assayed by measuring the value of R for the test sample, and the concentration of analyte in the test sample is determined by referring to the standard curve. As above, one standard curve can be generated and used for all test samples in a lot (e.g., for all test samples using a specified preparation of test reagents); it is not necessary that the standard curve be re-generated for each test sample. In another embodiment, the corrected analyte binding particle amount is determined as a ratio (R) of the amount of the analyte binding particle amount present in the sample capture zone, to the sum of the analyte binding particle amount present in the control capture zone and the analyte binding particle amount present in the sample capture zone. The amount of analyte present can be then determined from corrected analyte binding particle amount (the ratio), utilizing a standard curve. Alternatively, other ratios and/or standard curves can also be used to determine the amount of analyte in the sample. In addition, if desired, the amount of label that is present in the background can be subtracted from the analyte binding particle amount present in the sample capture zone and the analyte binding particle amount present in the control capture zone prior to calculation of the ratio (R).

"Competitive" or "Inhibition" Assays

The "competitive" or "inhibition" assay of the invention, like the "sandwich" assays, utilizes a solid phase apparatus including a membrane strip, as described above, that includes an application point, a sample capture zone, and a control capture zone. The membrane strip may optionally include a wicking pad following the control capture zone, and a sample pad preceding the application point. As before, the "application point" is the position on the membrane where a fluid sample is applied. This embodiment also utilizes a sample collection apparatus, as described above. The sample collection apparatus for the competitive (inhibition) assay contains a population of "analyte coated particles" which are coated with the analyte of interest (in lieu of being coated with an analyte binding agent, as described for the "sandwich" assays) or with an analog of the analyte of interest. An "analog" of the analyte, as used herein, is a compound that has similar binding characteristics as the analyte, in that is forms a binding pair with the analyte-binding agent as described above. The analyte or analog of the analyte can be coated directly on the particles, or can be indirectly bound to the particles. As used below, the term "analyte coated particles" can refer to particles that are coated either with analyte of interest or with an analog of the analyte of interest. As above with regard to the sandwich assay, the population of particles varies, depending on the size and composition of the particles, the composition of the membrane of the solid phase apparatus, and the level of sensitivity of the assay.

As above, the sample capture zone refers to a point on the membrane strip at which a sample capture reagent is immobilized. The sample capture reagent is an analyte binding agent, such as those described above. The sample capture reagent need not be the same analyte binding agent as described above; however, the sample capture reagent also forms a binding pair with the analyte of interest, in that it specifically and preferentially binds to the analyte of interest. As above, in a preferred embodiment, the sample capture reagent is an antibody directed against the analyte; it can be directed against the same epitope of the analyte as, or against a different epitope of the analyte from, the epitope that binds to the antibodies used as analyte binding agents coated on the particles.

The apparatus additionally includes a control capture reagent, as described above, that reacts with the analyte coated particles, but does not interact with the analyte to be measured: for example, the control capture reagent can react with another material on the particles (e.g., a carrier for the analyte that is bound to the particles; an antibody); or with the particles themselves. In a preferred embodiment, the sample capture reagent and the control capture agent are both antibodies. The control capture reagent is immobilized on the membrane (coated on and/or permeated in the membrane) in the control capture zone.

The components of the competitive assay are positioned in a similar manner as described above with regard to the "sandwich" assay. For example, in a preferred embodiment, the control capture zone is closely adjacent to the sample capture zone, so that the dynamics of the capillary action of the components of the assay are similar (e.g., essentially the same) at both the control capture zone and the sample capture zone; and yet the control capture zone and the sample capture zone are also sufficiently spaced such that the particles arrested in each zone can be quantitated individually. Furthermore, in a preferred embodiment, the sample capture zone is separated from the application point by a space that is a large distance, relative to the small distance between the sample capture zone and the control capture zone, in order to ensure that the speed of the capillary front is sufficiently slow to allow capture of particles, and the total time of migration is sufficiently long to allow for binding of analyte to the sample capture reagent.

To perform the competitive assay, a fluid sample to be assessed for the presence of the analyte of interest, as described above, is used. In one embodiment, the fluid sample is introduced into (drawn into, poured into, or otherwise placed into) the sample collection apparatus. For example, in one embodiment, the fluid sample is drawn up into a sample collection apparatus that comprises a pipette tip. Introduction of the fluid sample into the sample collection apparatus results in mixing of the fluid sample with the analyte coated particles, forming a "mixed fluid sample." If the analyte coated particles are evaporatively-, freeze- or vacuum-dried, the introduction of the fluid sample into the sample collection apparatus can result in rehydration and suspension of the analyte binding particles in the fluid sample. A buffer (e.g., as described above) is also introduced into the mixed fluid sample, forming a "buffered, mixed fluid sample." The buffered, mixed fluid sample can be formed either by dispensing the mixed fluid sample into a "buffer container" (e.g., test tube) containing the buffer, or by introducing the buffer into the sample collection apparatus prior to introducing the fluid sample. In another embodiment, the buffer is introduced into the sample collection apparatus, followed by introduction of the fluid sample into the sample collection apparatus. Alternatively, if the analyte of interest is a solid (e.g., a powder, a particulate; spore; or other particle, as described above), the fluid sample as described above can be prepared by introducing the solid into the buffer container; in this embodiment, the buffered, mixed fluid sample is formed by introducing the fluid sample (comprising the buffer) into the sample collection apparatus.

To disperse the analyte coated particles further into the fluid sample, if desired, the sample collection apparatus into which the fluid sample and the buffer has been introduced, or the buffer container into which the mixed fluid sample has been introduced, can be agitated (e.g., vortexed, shaken, pipetted down and up, etc.).

In a preferred embodiment, the sample collection apparatus comprises a pipette tip having vacuum-dried analyte coated particles within its tip; the fluid sample is drawn into the pipette, thereby rehydrating the dried analyte coated particles and forming a mixed fluid sample. In a particularly preferred embodiment, the mixed fluid sample is introduced into a buffer container, resulting in a buffered mixed fluid sample; the buffered mixed fluid sample in the buffer container is pipetted up and down using the sample collection apparatus, thereby further dispersing the analyte coated particles.

The buffered, mixed fluid sample is applied to the application point of the membrane strip of the solid phase apparatus, or to the application pad, if present. After the membrane strip is contacted with the buffered, mixed fluid sample, the membrane strip is maintained under conditions which allow fluid to move by capillary action to and through the membrane. The analyte coated particles (and analyte, if present in the sample) move through the membrane as a result of capillary action of the fluid from the buffered, mixed fluid sample, to and through the "sample capture zone" on the membrane and subsequently to and through the "control capture zone." The membrane strip is maintained under conditions (e.g., sufficient time and fluid volume) which allow the analyte coated particles to move by capillary action along the membrane to and through the sample capture zone and subsequently to the control capture zone, and subsequently beyond the capture zones (e.g., into a wicking pad), thereby removing any non-bound particles from the capture zones.

The movement of some of the analyte coated particles is arrested by binding of analyte coated particles to the sample capture reagent in the sample capture zone, and subsequently by binding of some of the analyte coated particles to the control capture reagent in the control capture zone. The analyte coated particles compete with analyte (if present) in the sample for binding to the sample capture reagent. The sample capture reagent binds to analyte coated particles by binding to analyte on the analyte coated particles. The term, "sample-reagent-analyte-coated-particle complexes", as used herein, refers to a complex of the sample capture reagent and analyte coated particles. The analyte coated particles are arrested in the sample capture zone, forming the sample-reagent-analyte-coated-particle complexes, due to capture of the analyte coated particles by interaction of the analyte on the particles with the sample capture reagent in the sample capture zone.

The control capture reagent binds to analyte coated particles by binding to any component of the analyte-coated particles except the analyte itself. The term, "control-reagent-analyte-coated particle complexes," as used above, refers to a complex of the control capture reagent and analyte coated particles. As above, the analyte coated particles are arrested in the control capture zone, forming the control-reagent-analyte-coated particle complexes, due to capture of the analyte coated particles by interaction of the analyte binding particles with the control capture reagent in the control capture zone.

Capillary action subsequently moves any analyte coated particles that have not been arrested in either the sample capture zone or the control capture zone, onwards beyond the control capture zone. In a preferred embodiment, the fluid moves any contacted analyte coated particles that have not been arrested in either capture zone into a wicking pad which follows the control capture zone.

The amount of analyte coated particles arrested in the sample capture zone is then detected. The analyte coated particles are detected using an appropriate means for the type of label used on the analyte coated particles. In a preferred embodiment, the amount of analyte coated particles is detected by an optical method, such as by measuring the amount of fluorescence of the label of the analyte-binding particles. The amount of analyte coated particles arrested in the control capture zone is detected in the same manner as the amount of analyte coated particles in the sample capture zone. In one embodiment, as described above, the amount of analyte coated particles is represented by a curve that is directly related to the amount of label present at positions along the solid phase (e.g., the membrane strip). For example, the amount of particles at each position on the membrane strip (e.g., at the sample capture zone and the control capture zone, and/or areas in between or adjacent to the sample capture zone and the control capture zone, and/or other areas of the membrane strip) can be determined and plotted as a function of the distance of the position along the membrane strip. The amount of particles can then be calculated as a function of the area under the curve, which is related to the amount of label present.

A corrected analyte coated particle amount is determined, and the amount of analyte can then be determined from the corrected analyte coated particle amount using appropriate calculation. The corrected analyte coated particle amount is based on the amount of analyte coated particles arrested in the sample capture zone and in the control capture zone. For example, in one embodiment, the corrected analyte coated particle amount is inversely proportional to a ratio (R) of the analyte-coated particle amount present in the sample capture zone to the analyte-coated particle amount present in the control capture zone. The amount of analyte present can be then determined from the corrected analyte coated particle amount (the ratio), utilizing a standard curve. The standard curve is generated by preparing a series of control samples, containing known concentrations of the analyte of interest in the fluid in which the analyte is to be detected (such as serum depleted of the analyte). The assay cam then performed on the series of control samples; the value of R is measured for each control sample; and the R values are plotted as a function of the concentration of analyte included in the control sample. Samples containing an unknown amount of analyte (the "test samples") are assayed by measuring the value of R for the test sample, and the concentration of analyte in the test sample is determined by referring to the standard curve. As above, one standard curve can be generated and used for all test samples in a lot (e.g., for all test samples using a specified preparation of test reagents); it is not necessary that the standard curve be re-generated for each test sample. In another embodiment, the corrected analyte coated particle amount is inversely proportional to a ratio (R) of the amount of the analyte coated particle amount present in the sample capture zone, to the sum of the analyte coated particle amount present in the control capture zone and the analyte coated particle amount present in the sample capture zone. The amount of analyte present can be then determined from corrected analyte coated particle amount (the ratio), utilizing a standard curve. Alternatively, other ratios and/or standard curves can also be used to determine the amount of analyte in the sample. In addition, if desired, the amount of label that is present in the background can be subtracted from the analyte coated particle amount present in the sample capture zone and the analyte coated particle amount present in the control capture zone prior to calculation of the ratio (R).

Benefits of the Invention

The methods of the invention provide assays with enhanced sensitivity, when compared with assays in which the analyte binding particles are imbedded within the membrane of the solid phase apparatus. For the sandwich assays, for example, because the fluid sample to be assayed for the analyte of interest is mixed with the analyte binding particles prior to application to the membrane, there is a longer time for the analyte of interest to bind to the analyte binding particles prior to the capture reaction which occurs in the membrane. Furthermore, because the interaction between the analyte of interest and the analyte binding particles occurs in the fluid phase, it allows more efficient binding because of greater mobility of the particles, than the same interaction between analyte of interest and analyte binding particles would be in the matrix of the membrane of the solid phase apparatus. Also, with regard to both the sandwich and the competitive assays, a greater number of particles can be included in a fluid collection apparatus than would be possible to embed in a solid phase apparatus; the greater number further enhances the sensitivity of the reaction. In addition, because the analyte binding particles (or analyte coated particles) are dispersed in the buffered, mixed fluid sample prior to application of the buffered, mixed fluid sample to the solid phase membrane, the particles pass over the capture zone(s) in a continuous manner through the capillary action of the fluid, rather than in a quick wave on the crest of a fluid front. As a result, a lower concentration of particles flows through the capture zone(s) for a longer time: thus the time during which particles can be "captured" is effectively increased, while the amount of particles that pass through the capture zone(s) is effectively lowered, thereby avoiding the blocking of capture of some particles by others which occurs when the particles pass on the crest of a fluid front.

Although the assays of the invention have been described particularly in relation to immunoassays, the assays can similarly be used with other binding pairs as described above (e.g., nucleic acids, receptor-ligands, lectin-sugars), using the same methods as described above with the desired components as the analyte and the and the analyte binding agent.

Kits of the Invention

The invention also includes kits for use in the methods described herein. Kit components can include: first and/or second members of a specific binding pair, buffers and/or buffer containers, fluid collection means, one or more solid phase apparatus (optionally comprising an application pad and/or wicking pad), at least one sample collection apparatus, one or more buffer containers, control samples for generation of a standard curve and/or other standard curve information, analyte binding particles, analyte coated particles, and/or control particles, capture reagents, antibodies, tools to assist in collecting of samples to be assessed for analyte of interest (e.g., swabs), disposal apparatus (e.g., biohazard waste bags), and/or other information or instructions regarding the sample collection apparatus (e.g., lot information, expiration date, etc.). For example, in one embodiment, a kit comprises at least one sample collection apparatus having analyte binding particles within it; in a preferred embodiment, a kit comprises at least one pipette tip having evaporatively-dried, vacuum-dried or freeze-dried analyte binding particles therein. In another embodiment, a kit comprises at least one solid phase apparatus as described herein and at least one sample collection apparatus. In another preferred embodiment, a kit comprises at least one pipette; at least one or more pipette tips having evaporatively-dried, vacuum-dried or freeze-dried analyte binding particles therein; and at least one solid phase apparatus. This preferred embodiment can also optionally contain information regarding the standard curve, lot information, and/or expiration date relating to the analyte binding particles in the pipette tips. In yet another preferred embodiment, a kit comprises at least one sample collection apparatus; at least one pipette tip having dried analyte binding particles thereon; at least one solid phase apparatus; and at least one buffer container. This preferred embodiment can also optionally contain buffer within the buffer container; and tool (e.g., a swab) for collection of a solid sample.

The invention is further illustrated by the following examples, which are not intended to be limiting in any way.

EXAMPLE 1

Titration of Latex into Buffer, Compared With Control Strips

Materials and Methods

Experiments were set up as follows. To prepare the solid phase apparatus ("test cartridge"), nitrocellulose membrane pre-attached to Mylar backing was used. A specific antibody (sample capture reagent) was applied to the membrane at the sample capture zone, and an internal control antibody (control capture reagent) was applied to the membrane at the control capture zone. After the antibodies were applied, the protein binding sites on the membrane were blocked by treatment with Poly Vinyl Alcohol (PVA), and then the membranes were washed and dried. The membrane was then cut into 5 mm wide strips, perpendicularly to the lines of antibody applied. The strips were then assembled into test cartridges (solid phase apparatus) along with two pads: a) an application pad at the proximal end that functions as a filter to separate blood cells (if whole blood is used), or alternatively, a glass fiber pad (to act as a sample holding pad for the anthrax test); and b) a wicking pad at the distal end (beyond the antibody lines) of glass fiber to act as an absorbent pad to soak up fluid that travels through the membrane from the proximal end where the sample is added to the distal end.

The test cartridge was press fit together with an opening in the cartridge and a "well" above the sample pad, pressing into the pad, so that a liquid sample was retained until it could be absorbed into the pad and membrane. The bottom of the cartridge had a "window" where the membrane lower surface (the Mylar backing) is exposed so that optical readings can be taken after the test is run. There were no other openings in the cartridge, although it was not hermetically sealed. The cartridge was desiccated and then sealed into a foil pouch with a small desiccant pouch.

The pipette tip (sample collection apparatus) was configured as follows: commercially available pipette tips for use with automatic pipettes of various types were placed into a rack that holds them in a vertical orientation a 12×8 matrix with 9 mm centers. An automated system delivered 5 microliters of an antibody-coated, dyed latex suspension into each tip. The suspension was delivered as a small (2 mm) dot about 1 cm from the small end of the tip. The suspension was in a solution of trehalose (sugar), in order to make the suspension viscous so that it stays in place when delivered to the tip; to help stabilize the protein when it is dried; and to act as a "glue" so that the dried spot stays in place. The tips were then dried under vacuum conditions, and once dried, were placed into the same pouch as the cartridge (one of each) prior to sealing.

Buffer vials were configured as follows: the buffer vial had a tight fitting cap and contained a pre-measured amount of diluent. Once the diluent vial was filled, it was capped and put into the test kit. The amount and composition of the buffer varied for each different type of assay. The quantity was adjusted so that the sample is diluted to a level that is appropriate for each test. For instance, a myoglobin test uses a 1:10 dilution of blood, the troponin I test uses a 1:3 dilution of blood. The anthrax test uses sufficient buffer to suspend the sample and latex after losses in the test are accounted for. The buffer can be water based and include several different salts, buffers and detergents. For example, representative buffers for representative analytes include the following: for myoglobin, a buffer including 122 mM PB, 100 mM NaCl, 3.3% BSA, 1.1% Cremophor EL, 0.05% ProClin300, pH 7.2 can be used; for CKMB, a buffer including 115 mM PB, 115 mM NaCl, 2.3% BSA, 0.25% Surfynol 104PG-50, 0.3% Casein, 40 mM Phe, 0.5% Sheep serum, 0.05% ProClin 300, pH 7.2 can be used; for TnI, a buffer including 124 mM PB, 124 mM NaCl, 3.24% BSA, 0.76% Surfactant 10G, 0.54% casein, 405 mM GHCl, 40 mM Phe, 10% Goat serum, pH 7.2 can be used; for anthrax, a buffer including 138 mM PB, 138 mM NaCl, 3.6% BSA, 0.84% Surfactant 10G, 0.6% casein, 0.05% High viscosity Methyl cellulose, 0.05% ProClin 300, pH 7.2 can be used (abbreviations: PB=Phosphate Buffer, NaCl=Sodium Chloride, BSA=Bovine Serum Albumin, Phe=Phenylalanine).

To perform the assay for a blood sample, the following procedure was followed:

A sample of blood was pipetted into the buffer vial, either with any type of pipette OR with the pipette tip with the latex dot (sample collection apparatus). This was a simple liquid transfer operation. The pipette tip with the latex dot was then used to mix the sample and buffer, by repeatable pipetting the liquid up and down at least 10 times. During this mixing operation, the liquid came into contact with the latex dot and caused it to rehydrate and become suspended in the diluent-sample matrix. Once suspended, the antibody on the latex began to bind to antigen (if present) in the sample. The pipette (with the same tip as above) was then used to transfer a portion of the buffered mixture to the sample well in the cartridge. The cartridge was then placed into the reader where the following occurs: a) the diluent began to soak into the sample pad where blood calls are retained. The liquid flowed through the pad and contacted the nitrocellulose membrane. The liquid (with suspended latex) flowed by capillary action along the length of the membrane to the absorbent pad which becomes wetted. When the latex reached the test line (sample capture zone), if there is any antigen in the sample some would be captured by the immobilized antibody (sample capture reagent). If the antigen had also been bound by the antibody on the latex, the latex would also be captured, by virtue of the antigen being sandwiched between the two antibodies. Latex that was not captured at the test line continued to flow and next encountered the internal control antibody line (control capture zone). This antibody was directed towards the material (antibody or other material) on the latex itself. A portion of the latex was captured at the internal control line due to this capture reaction. The remaining liquid and unbound latex continued to the distal end of the strip and was retained in the wicking pad. The liquid flow stopped when the pad is saturated OR when the sample was fully absorbed into the sample pad and capillary pressure was equilibrated. The reader then determined the amount of latex at the test line and in the internal control line and applied a ratio method to determine the quantity of antigen in the sample by comparison to a standard curve determined for that lot of test cartridges.

To run the assays for samples with particulate antigens (i.e. anthrax spores), samples are taken as follows. If the material is to be samples from a surface (e.g., a table top) the following procedure was used: a swab was introduced into the buffer vial to dampen the swab tip; the swab was then used to gently scrub the surface to be tested; the swab was then put back into the buffer vial and twirled to allow release of the particulate material into the diluent; the swab was removed and discarded. The test procedure above was then followed. If the material to be tested was in liquid form (e.g., a liquid suspension of particles) the following was performed: a sample (10 to 30 microliters) of the test liquid was applied to the dry swab OR the dry swab was immersed into the test liquid; the Swab was then immersed in the diluent liquid and gently twirled to release the particles; the swab was removed and discarded. The test procedure was followed as above. If the material to be tested was in powder or granular form the following was performed: a small sample of the powder was added to the diluent by either scooping a small amount of the material into the vial OR by touching a wet or dry swab tip to the powder and then placing it into the vial of diluent. The test procedure was followed as above.

Results

Using the methods described above, assays were run to compare results obtained by titrating latex particles into buffer (diluent) using dried latex in pipette tips, with results obtained by coating latex particles onto the membrane strips (at a latex application site "LAS") and allowing the fluid of the sample to move by capillary action through the LAS prior to movement through the sample capture zone and the control capture zone. The samples were horse serum standards and blood M5 at baseline (0) and 0.5 ng/ml TnI. The buffer (diluent) was TnI diluent with 200 mM GHCl+10% goat serum, with 0, 0.5×, 1×, 2×, 4×, or 8× latex particles. Results are shown in Table 1.

TABLE 1

Effect of Titrating Latex Particles in Pipette with Buffer, Compared with Latex Particles at LAS on Membrane Strip

| Diluent/Strips | Conc | R10 | SD | CV | S:B R10 | S-B R10 |
|---|---|---|---|---|---|---|
| Horse Serum Standards R10 Values | | | | | | |
| Control | 0 | 0.041 | 0.006 | 15.1% | 1.32 | 0.003 |
| with LAS strips | 0.5 | 0.054 | 0.004 | 6.6% | | |
| 0.5× Latex | 0 | 0.036 | 0.004 | 11.9% | 1.98 | 0.030 |
| with no LAS strips | 0.5 | 0.071 | 0.001 | 1.8% | | |
| 1× Latex | 0 | 0.040 | 0.001 | 1.3% | 1.90 | 0.031 |
| with no LAS strips | 0.5 | 0.076 | 0.004 | 5.9% | | |
| 2× Latex | 0 | 0.049 | 0.002 | 3.6% | 1.83 | 0.032 |
| with no LAS strips | 0.5 | 0.090 | 0.007 | 8.1% | | |
| 4× Latex | 0 | 0.065 | 0.001 | 2.3% | 1.71 | 0.035 |
| with no LAS strips | 0.5 | 0.110 | 0.009 | 8.1% | | |
| 8× Latex | 0 | 0.101 | 0.003 | 2.6% | 1.39 | 0.034 |
| with no LAS strips | 0.5 | 0.141 | 0.002 | 1.7% | | |
| Blood M5 R10 Values | | | | | | |
| Control | 0 | 0.040 | 0.007 | 16.8% | 1.35 | 0.003 |
| with LAS strips | 0.5 | 0.054 | 0.004 | 7.4% | | |
| 0.5× Latex | 0 | 0.029 | 0.001 | 5.0% | 1.85 | 0.023 |
| with no LAS strips | 0.5 | 0.054 | 0.001 | 1.3% | | |
| 1× Latex | 0 | 0.033 | 0.001 | 4.4% | 2.19 | 0.033 |
| with no LAS strips | 0.5 | 0.073 | 0.005 | 6.4% | | |
| 2× Latex | 0 | 0.049 | 0.006 | 13.3% | 1.78 | 0.028 |
| with no LAS strips | 0.5 | 0.087 | 0.004 | 4.5% | | |
| 4× Latex | 0 | 0.082 | 0.010 | 12.7% | 1.66 | 0.032 |
| with no LAS strips | 0.5 | 0.135 | 0.011 | 8.5% | | |
| 8× Latex | 0 | 0.158 | 0.006 | 3.8% | 1.33 | 0.030 |
| with no LAS strips | 0.5 | 0.210 | 0.016 | 7.4% | | |

It was observed that using the latex diluents at 0.5×, 1×, 2×, and 4× resulted in a significant increase in signal:background (S:B) compared to the control LAS strips. The increase in S:B was due to an increase in specific binding of the positive sample and similar background of the zero sample. This resulted in an increase in sensitivity of the system. As the amount of latex increased, the raw TL and ISL signals increased accordingly. The 1× latex diluent gave comparable TL and ISL signals to the control LAS strips. Thus, it was concluded that the latex diluent gave higher sensitivity than the control LAS strips in RAMP assays.

EXAMPLE 2

Comparison of 1× Latex Diluent vs. LAS Strips in Standard Curve

Using the methods described above in Example 1, assays were run to compare results obtained by titrating latex particles into buffer (diluent) using dried latex in pipette tips, with results obtained by coating latex particles onto the membrane strips (at a latex application site "LAS") as described above. The samples were horse serum standards and blood M35 spiked at 0, 0.1, 0.2, 0.5, 1 and 3 ng/ml. The buffer (diluent) was TnI diluent with 180 mM GHCl+10% goat serum, with or without 1× latex particles. Results are shown in Table 2.

TABLE 2

Full Standard Curves in Horse Serum and Blood Using 1X Latex Particle Diluent and Full Length Membrane Strips

| Sample | TnI Conc | R10 | SD | CV | R10 S:B | R10 S-B |
|---|---|---|---|---|---|---|
| R10 Values—1X Latex Diluent with No LAS Strips (Full-length) | | | | | | |
| HS Stds | 0.0 | 0.018 | 0.001 | 5.6% | — | — |
|  | 0.1 | 0.026 | 0.002 | 8.3% | 1.45 | 0.005 |
|  | 0.2 | 0.030 | 0.001 | 2.7% | 1.66 | 0.010 |
|  | 0.5 | 0.049 | 0.001 | 1.7% | 2.72 | 0.029 |
|  | 1.0 | 0.071 | 0.003 | 3.8% | 3.92 | 0.049 |
|  | 3.0 | 0.164 | 0.013 | 8.0% | 9.03 | 0.131 |
| Blood M35 | 0.0 | 0.017 | 0.002 | 10.1% | — | — |
|  | 0.1 | 0.023 | 0.002 | 7.7% | 1.37 | 0.003 |
|  | 0.2 | 0.026 | 0.001 | 5.3% | 1.55 | 0.006 |
|  | 0.5 | 0.043 | 0.003 | 5.9% | 2.50 | 0.021 |
|  | 1.0 | 0.064 | 0.003 | 4.2% | 3.74 | 0.042 |
|  | 3.0 | 0.145 | 0.008 | 5.4% | 8.55 | 0.119 |
|  |  |  | Avg CV | 5.7% |  |  |
| R10 Values—Control Diluent (no Latex) with Control strips (with LAS) | | | | | | |
| HS Stds | 0.0 | 0.034 | 0.001 | 2.5% | — | — |
|  | 0.1 | 0.044 | 0.002 | 4.7% | 1.31 | 0.007 |
|  | 0.2 | 0.042 | 0.004 | 10.0% | 1.24 | 0.003 |
|  | 0.5 | 0.054 | 0.005 | 8.3% | 1.62 | 0.015 |
|  | 1.0 | 0.063 | 0.008 | 12.1% | 1.89 | 0.021 |
|  | 3.0 | 0.106 | 0.010 | 9.5% | 3.14 | 0.061 |
| Blood M35 | 0.0 | 0.029 | 0.002 | 7.8% | — | — |
|  | 0.1 | 0.035 | 0.005 | 13.6% | 1.19 | -0.001 |
|  | 0.2 | 0.033 | 0.003 | 9.8% | 1.13 | -0.002 |
|  | 0.5 | 0.042 | 0.002 | 5.1% | 1.46 | 0.009 |
|  | 1.0 | 0.055 | 0.003 | 5.1% | 1.89 | 0.021 |
|  | 3.0 | 0.101 | 0.006 | 5.7% | 3.50 | 0.064 |
|  |  |  | Avg CV | 8.3% |  |  |

It was observed that the 1× latex diluent resulted in a consistent increase in S:B over an entire standard curve range in both diluent and blood samples compared to the control LAS strips. The improved sensitivity was observed not only in the higher S:B but also in the discrimination of the 0.1 ng/ml point from zero in blood using the latex diluent whereas with the LAS strips, there was not clear discrimination from zero until 0.5 ng/ml. These results confirmed the significant improvement in sensitivity of the RAMP system using latex diluent compared to LAS strips.

EXAMPLE 3

Titration of Latex Diluent vs. Control LAS Strips

Using the methods described above in Example 1, assays were run to compare results obtained by titrating latex particles into buffer (diluent) using dried latex in pipette tips, with results obtained by coating latex particles onto the membrane strips (at a latex application site "LAS") as described above. The samples were 0 and 2000 ng/ml anthrax spores (*Bacillus anthracis*). The buffer (diluent) was TnI diluent with or without 1×, 3× or 6× latex particles. Results are shown in Table 3.

TABLE 3

Assay for Anthrax Using Latex Particle Diluent and Full Length Membrane Strips
BA Samples
R10 Values

| Diluent/Strips | Conc | R10 | SD | CV | S:B R10 | S-B R10 |
|---|---|---|---|---|---|---|
| Control Diluent (No latex) | 0 | 0.010 | 0.001 | 11.3% | 1.54 | 0.002 |
| with LAS strips | 2000 | 0.016 | 0.003 | 17.2% | | |
| 1x Latex Diluent | 0 | 0.026 | 0.008 | 30.8% | 2.46 | 0.030 |
| with no LAS strips | 2000 | 0.064 | 0.000 | 0.0% | | |
| 3x Latex Diluent | 0 | 0.018 | 0.002 | 11.1% | 3.28 | 0.036 |
| with no LAS strips | 2000 | 0.059 | 0.003 | 5.1% | | |
| 6x Latex Diluent | 0 | 0.020 | 0.001 | 5.0% | 3.30 | 0.040 |
| with no LAS strips | 2000 | 0.066 | 0.005 | 7.6% | | |

It was observed that using the latex diluent at 1×, 3×, and 6× results in a significant increase in S:B compared to the control LAS strips for the anthrax assay. The S:B were higher for the 3× and 6× latex diluents than the 1× latex diluent. These results confirmed that the improvement in sensitivity of the RAMP system using latex diluent compared to LAS strips applied to the anthrax assay.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for quantitatively measuring the amount of an analyte of interest in a fluid sample, comprising:
   a) providing a solid phase apparatus comprising a membrane strip comprising an application point, a sample capture zone and a control capture zone, wherein the sample capture zone is between the application point and the control capture zone;
   b) providing a sample collection apparatus containing a population of analyte coated particles, wherein the analyte coated particles are coated with analyte or an analog of the analyte, and wherein the sample collection apparatus is not in fluid communication with the solid phase apparatus;
   c) either i) introducing the fluid sample into the sample collection apparatus, producing a mixed fluid sample, and subsequently introducing a buffer into the mixed fluid sample; ii) introducing a buffer into the sample collection apparatus and subsequently introducing the fluid sample; or iii) forming the fluid sample by introducing a solid into a buffer, and subsequently introducing the fluid sample into the sample collection apparatus, thereby producing a buffered, mixed fluid sample comprising analyte coated particles;
   d) applying the buffered, mixed fluid sample to the application point of the membrane strip;
   e) maintaining the membrane strip under conditions which allow fluid to transport analyte coated particles by capillary action through the strip to and through the sample capture zone, the sample capture zone having a sample capture reagent immobilized thereon; and allow analyte coated particles to bind to the sample capture reagent;
   f) further maintaining the membrane strip under conditions which allow the fluid in the sample to transport analyte coated particles by capillary action through the strip to and through the control capture zone, the control capture zone having a control capture reagent immobilized thereon; and allow analyte coated particles to bind to the control capture reagent;

g) further maintaining the membrane strip under conditions which allow the fluid in the sample to transport any analyte coated particles not bound to the sample capture reagent or to the control capture reagent by capillary action beyond the control capture zone;

h) determining the amount of analyte coated particles in the sample capture zone and the amount of analyte coated particles in the control capture zone;

i) determining a corrected analyte coated particle amount from the amount of analyte coated particles in the sample capture zone and the amount of analyte coated particles in the control capture zone, wherein the amount of analyte of interest in the fluid sample is inversely related to the corrected analyte coated particle amount.

2. The method of claim 1, wherein the corrected analyte coated particle amount is determined as a ratio of the amount of analyte coated particles in the sample capture zone, to the amount of analyte coated particles in the control capture zone.

3. The method of claim 1, wherein the corrected analyte coated particle amount is determined as a ratio of the amount of analyte coated particles in the sample capture zone, to the sum of the amount of analyte coated particles in the control capture zone and the amount of analyte coated particles in the sample capture zone.

4. The method of claim 1, wherein the membrane strip is made of cellulose nitrate or glass fiber.

5. The method of claim 1, wherein the particles are latex beads.

6. The method of claim 1, wherein the particles are labeled.

7. The method of claim 6, wherein the label is selected from the group consisting of: colorimetric, fluorescent, phosphorescent, luminescent, chemiluminescent, and enzyme-linked molecule.

8. The method of claim 1, wherein the analyte and the sample capture reagent are members of a binding pair, and one member of the binding pair is selected from the group consisting of: a spore, a protein, a hormone, an enzyme, a glycoprotein, a peptide, a small molecule, a polysaccharide, a lectin, an antibody, an antibody fragment, a nucleic acid, a drug, a drug conjugate, a toxin, a virus, a virus particle, a portion of a cell wall, a hapten, and a receptor.

9. The method of claim 1, wherein the sample capture reagent is selected from the group consisting of: an antibody; an antibody fragment; a hapten; a drug conjugate; and a receptor.

10. The method of claim 9, wherein the sample capture reagent is an antibody.

11. The method of claim 9, wherein the control capture reagent is an anti-immunoglobulin antibody.

12. The method of claim 1, wherein the fluid sample is selected from the group consisting of: whole blood, plasma, serum, urine, cerebrospinal fluid, saliva, semen, vitreous fluid, and synovial fluid.

13. The method of claim 1, wherein the fluid sample comprises a suspended solid.

14. The method of claim 13, wherein the solid is selected from the group consisting of: a particulate sample, a powder sample, a soil sample, and spores.

15. The method of claim 14, wherein the spores comprise spores of *Bacillus anthracis*.

16. The method of claim 1, wherein the fluid sample is selected from the group consisting of: water, groundwater, sewage, and waste water.

17. The method of claim 1, wherein the analyte of interest is selected from the group consisting of: myoglobin, CK-MB, troponin I, and PSA.

18. The method of claim 1, wherein in step (d) the mixed fluid sample is applied to the application point through an application pad.

19. The method of claim 1, wherein in step (g) the fluid in the sample transports any analyte coated particles not bound to the sample capture reagent or to the control capture reagent by capillary action beyond the control capture zone into a wicking pad.

20. The method of claim 1, wherein the sample collection apparatus is selected from the group consisting of: a pipette and a pipette tip.

21. The method of claim 1, wherein the population of analyte coated particles are evaporatively-dried, vacuum-dried or freeze-dried.

22. A method for quantitatively measuring the amount of an analyte of interest in a fluid sample, comprising:

a) providing a solid phase apparatus comprising a membrane strip comprising an application point, a sample capture zone and a control capture zone, wherein the sample capture zone is between the application point and the control capture zone;

b) providing a pipette containing a population of analyte coated particles, wherein the analyte coated particles are coated with analyte or an analog of the analyte, and wherein the pipette is not in fluid communication with the solid phase apparatus;

c) either i) introducing the fluid sample into the pipette, producing a mixed fluid sample, and subsequently introducing a buffer into the mixed fluid sample; ii) introducing a buffer into the pipette and subsequently introducing the fluid sample; or iii) forming the fluid sample by introducing a solid into a buffer, and subsequently introducing the fluid sample into the sample collection apparatus, thereby producing a buffered, mixed fluid sample comprising analyte coated particles;

d) applying the buffered, mixed fluid sample to the application point of the membrane strip;

e) maintaining the membrane strip under conditions which allow fluid to transport analyte coated particles by capillary action through the strip to and through the sample capture zone, the sample capture zone having a sample capture reagent immobilized thereon; and allow analyte coated particles to bind to the sample capture reagent;

f) further maintaining the membrane strip under conditions which allow the fluid in the sample to transport analyte coated particles by capillary action through the strip to and through the control capture zone, the control capture zone having a control capture reagent immobilized thereon; and allow analyte coated particles to bind to the control capture reagent;

g) further maintaining the membrane strip under conditions which allow the fluid in the sample to transport any analyte coated particles not bound to the sample capture reagent or to the control capture reagent by capillary action beyond the control capture zone;

h) determining the amount of analyte coated particles in the sample capture zone and the amount of analyte coated particles in the control capture zone;

i) determining a corrected analyte coated particle amount from the amount of analyte coated particles in the sample capture zone and the amount of analyte coated particles in the control capture zone, wherein the amount of analyte of interest in the fluid sample is inversely related to the corrected analyte coated particle amount.

* * * * *